US009074237B2

(12) United States Patent
Timmins et al.

(10) Patent No.: US 9,074,237 B2
(45) Date of Patent: Jul. 7, 2015

(54) METHOD FOR DIAGNOSING *FRANCISELLA TULARENSIS* INFECTION

(75) Inventors: Graham Timmins, Albuquerque, NM (US); Terry Wu, Albuquerque, NM (US); Seong Won Choi, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/111,066

(22) PCT Filed: Apr. 12, 2012

(86) PCT No.: PCT/US2012/033260

§ 371 (c)(1), (2), (4) Date: Oct. 10, 2013

(87) PCT Pub. No.: WO2012/142246

PCT Pub. Date: Oct. 18, 2012

(65) Prior Publication Data

US 2014/0212916 A1 Jul. 31, 2014

Related U.S. Application Data

(60) Provisional application No. 61/517,072, filed on Apr. 13, 2011.

(51) Int. Cl.

| | |
|---|---|
| *C12Q 1/34* | (2006.01) |
| *C12Q 1/04* | (2006.01) |
| *C07C 275/16* | (2006.01) |
| *C07B 59/00* | (2006.01) |

(52) U.S. Cl.

CPC .............. *C12Q 1/04* (2013.01); *C12Q 2304/46* (2013.01); *C12Q 2304/48* (2013.01); *C07B 2200/05* (2013.01); *C07C 275/16* (2013.01); *C07B 2200/07* (2013.01); *C07B 59/001* (2013.01)

(58) Field of Classification Search

USPC .......................................................... 435/34

See application file for complete search history.

(56) References Cited

U.S. PATENT DOCUMENTS

2003/0199102 A1 10/2003 Ostrup
2008/0287774 A1* 11/2008 Katz-Brull .................... 600/414
2009/0191639 A1 7/2009 Timmins

FOREIGN PATENT DOCUMENTS

WO 2011024156 A1 3/2011

OTHER PUBLICATIONS

Mahawar M. et al. Contribution of Citrulline Ureidase to *F. tularensis* Strain Schu S4 Pathogenesis. J of Bacteriology 191(15)4798-4806, Aug. 2009.*

Jassal M. 13C Urea Breath Test as a Novel Point of Care Biomarker for TB Treatment and Diagnosis. PloS One 5(8)e12451 Aug. 27, 2010.*

Zhu T, et al. The expression, purification and activity analysis of Francisella tularensis citrulline ureidase in *Escherichia coli*. J. Appl. Biomed, 2014, http://dx.doi.org/010.1016/j.jab.2014.11.003.

Marchette NJ, Nicholes PS. Virulence and Citrulline Ureidase Activity of Pasteurella Tularensis. J Bacteriol, 1961;62:26-32.

Fleming De, Foshay L. Studies on the Physiology of Virulence of Pasteurella Tularensis. J Bacteriol, 1955;70:345-349.

Larsson P, et al. The complete genome sequence of *Francisella tularensis*, the causative agent of tularemia. Nature Genetics, 2005;37(2):153-159.

* cited by examiner

*Primary Examiner* — Ralph Gitomer

(74) *Attorney, Agent, or Firm* — Henry D. Coleman; R. Neil Sudol

(57) ABSTRACT

The present invention is directed to the use of isotopically labeled citrulline for gnosing the presence or absence of a bacterial infection in the lungs of a patient.

17 Claims, 1 Drawing Sheet

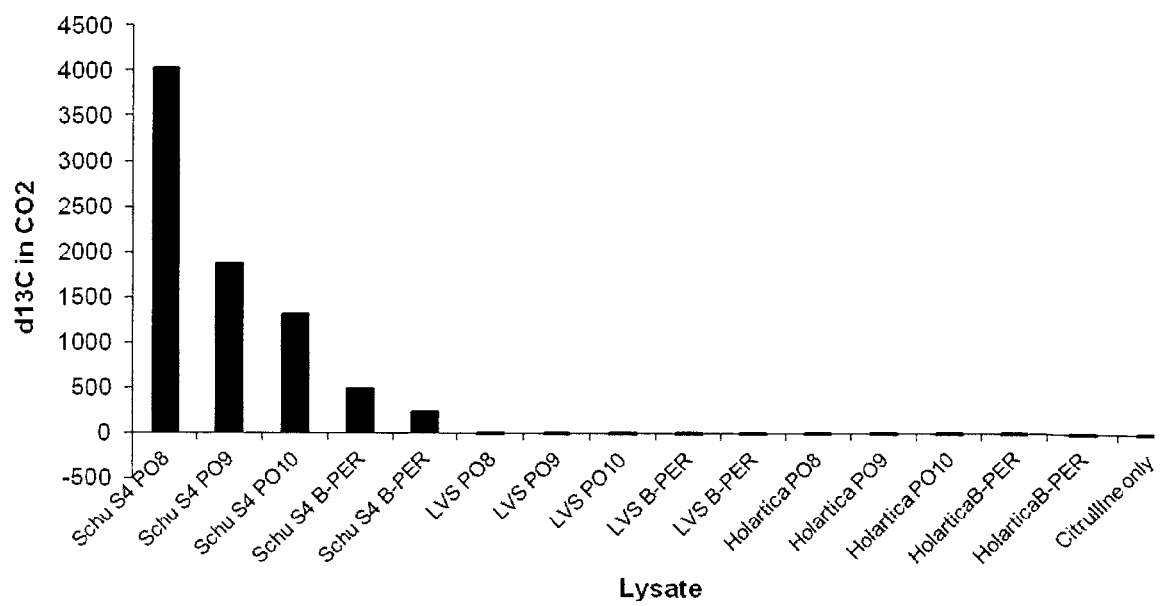

METHOD FOR DIAGNOSING *FRANCISELLA TULARENSIS* INFECTION

CROSS REFERENCE TO RELATED APPLICATIONS

This application is a U.S. national stage application of and claims priority from International Patent Application No. PCT/2012/033260 filed 12 Apr. 2012, which claims the benefit of U.S. Provisional Application No. 61/517,072, filed Apr 13, 2011, the entirety of which two applications is incorporated herein.

This application claims the benefit of U.S. Provisional Application No. 61/517,072, filed Apr. 13, 2011, the entirety of which is incorporated herein.

TECHNICAL FIELD

This invention relates to a rapid and effective test for detecting and diagnosing bacterial lung infections in patients using isotopically labeled citrulline, or a pharmaceutically acceptable salt thereof.

BACKGROUND

Bacterial infections of the lungs can be life threatening if left untreated. For example, pneumonic tularemia can be fatal if not properly treated. *Francisella tularensis* is a bacteria that can result in a pneumonic tularemia infection if inhaled. *F. tularensis* is so infectious that is has been identified by the Centers for Disease Control as a potential biological warfare agent.

Many bacterium have more that one biovar, i.e., more than one strain. *F. tularensis* has biovars, for example, Type A (Schu S4) and Type B (holarctica). Type A results in a more severe infection than Type B. Early detection of lung infections results in earlier treatment intervention and better prognosis for recovery. In addition, distinguishing between bacterial biovars allows for health care practitioners to prescribe the most appropriate treatment. As such, methods of detecting lung infections, and methods of distinguishing biovars of an infection, are needed.

SUMMARY

Methods for diagnosing the presence or absence of a bacterial infection in the lungs of a patient are described. These methods comprise administering an effective amount of an isotopically-labeled citrulline, or a pharmaceutically acceptable salt thereof, to the lungs of the patient; collecting one or more breath, urine, whole blood, plasma, or serum samples from the patient; and analyzing the one or more samples to determine the amount of isotopically labeled carbon dioxide, isotopically labeled ammonia, or a mixture thereof in said samples; said amount indicating the presence or absence of the bacterial infection.

Compositions and kits for use with the methods of the invention are also described.

BRIEF DESCRIPTION OF DRAWINGS

FIG. 1 depicts the amount of $^{13}C$ in headspace after treatment of strains of *Franscisella tularensis* with ureido $^{13}C$-citrulline.

DETAILED DESCRIPTION OF ILLUSTRATIVE EMBODIMENTS

The present invention is a breath test which can be used to detect the presence of a bacterial infection in the lungs of a patient. Certain bacteria have enzymes that can convert certain compounds into cleavage or fermentation products. Certain bacteria can convert citrolline into cleavage or fermentation products. It is theorized that an enzyme referred to as "citrulline ureidase" is responsible for the conversion of citrolline into cleavage or fermentation products. Certain strains of *Franscisella tularensis*, for example Type A (Schu S4), have this enzyme.

For example, citrulline is converted by citrulline ureidase to 2,5-diamino-pentanoic acid, carbon dioxide, and ammonia according to Scheme 1:

Scheme 1 citrulline $\xrightarrow{\text{citrulline ureidase}}$ + $CO_2$ + $NH_3$

It has now been discovered by the applicants that if isotopically labeled citrulline is administered to a patient having a bacterial infection, for example, a *Franscisella tularensis* infection, wherein the bacteria can convert citrulline to cleavage or fermentation products, isotopically labeled carbon dioxide and/or isotopically labeled ammonia is generated by the conversion of citrulline by citrulline ureidase. See Schemes 2 and 3.

Scheme 2

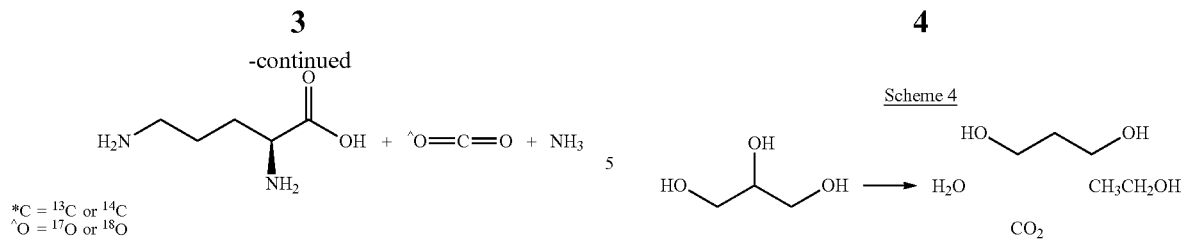

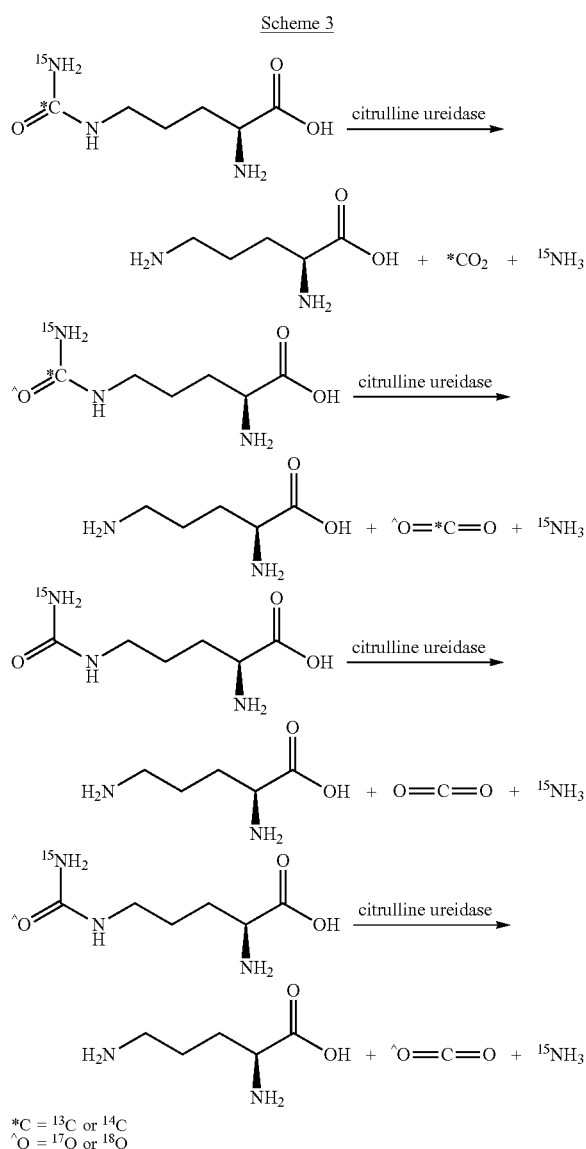

The applicants have also discovered that certain bacteria can convert glycerol into cleavage or fermentation products, for example, water, carbon dioxide, propane diol, and ethanol. See Scheme 4. It has heretofore been discovered that if isotopically labeled glycerol is administered to a patient having a bacterial infection wherein the bacteria can convert glycerol to cleavage or fermentation products, isotopically labeled water, isotopically labeled carbon dioxide, isotopically labeled propanediol, and/or isotopically labeled ethanol, depending on the type and location of the isotopic label, will be produced.

This isotopically labeled ammonia, carbon dioxide, water, propanediol, and ethanol generated by the cleavage and/or fermentation of isotopically labeled citrulline and/or isotopically labeled glycerol can be detected in the breath, urine, whole blood, plasma or serum samples from the patient who has been administered isotopically labeled citrulline and/or isotopically labeled glycerol. By measuring the amount, for example, the concentration, of isotopically labeled cleavage or fermentation product of citrulline, for example, isotopically labeled carbon dioxide or isotopically labeled ammonia, it is possible to determine whether the patient has a bacterial infection. Moreover, using the methods described herein, it is possible to identify the biovar of the bacterial infection. By using the methods of the invention, bacterial infections can readily be identified and appropriate treatment can be administered.

The present invention is directed to methods for diagnosing the presence or absence of a bacterial infection in the lungs of a patient comprising administering an effective amount of an isotopically-labeled citrulline, or a pharmaceutically acceptable salt thereof, to the lungs of the patient; collecting one or more breath, urine, whole blood, plasma, or serum samples from the patient; and analyzing the one or more samples to determine the amount of isotopically labeled carbon dioxide, isotopically labeled ammonia, or a mixture thereof in said samples; said amount indicating the presence or absence of the bacterial infection.

The isotopically labeled citrulline, or pharmaceutically acceptable salt thereof, used within the scope of the invention comprises $^{13}C$, $^{14}C$, $^{17}O$, $^{18}O$, $^{15}N$, $^{2}H$, or mixture thereof, wherein the $^{13}C$, $^{14}C$, $^{17}O$, $^{18}O$, $^{15}N$, $^{2}H$, is present in an amount greater than natural abundance. In some embodiments, the citrulline, or pharmaceutically acceptable salt thereof, includes a plurality of isotopic labels. Preferably, the isotopic label is $^{13}C$, $^{17}O$, $^{18}O$, $^{15}N$, or a mixture thereof. More preferably, the isotopic label is $^{13}C$ or $^{15}N$. Even more preferably, the isotopic label is $^{13}C$.

Isotopically labeled citrulline and isotopically labeled glycerol can be prepared according to methods known in the art. For example, one isotopically labeled citrulline of the invention can be prepared according to the following Scheme 5.

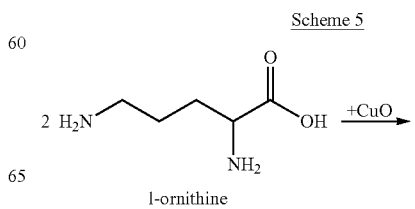

-continued

[Chemical structure: H₂N-substituted ornithine coordinated with Cu, forming a complex with NH and NH₂ groups]

[Chemical structure showing Cu complex with two ornithine-like ligands and urea (H₂N-¹³C(O)-NH₂) reacting]

[Chemical structure: Cu complex with ¹³C-labeled urea moiety attached]

[Chemical structure showing Al₂S₃ reacting to give 2 H₂N-¹³C(O)-NH-(CH₂)₃-CH(NH₂)-COOH + copper sulfide]

According to preferred embodiments of the invention, the isotopically labeled citrulline is delivered to the lungs of the patient by a pulmonary route of administration. For example, the isotopically labeled citrulline can be administered via aerosol inhalation or intratracheal instillation. Alternatively, the isotopically labeled citrulline can be administered orally. Those skilled in the art will readily understand that the amount of time between citrulline administration and bodily fluid collection will vary depending on the mode of administration of the citrulline.

In preferred embodiments of the invention, a breath sample is collected from the patient. The breath sample can be taken for a predetermined time to ensure that an adequate sample can be collected for analysis.

Predetermined breath sample volumes can also be collected to ensure that an adequate sample is collected for analysis.

In preferred embodiments of the invention, the breath sample, or other bodily fluid sample, will be analyzed for the presence of isotopically labeled carbon dioxide. Preferably, the isotopically labeled carbon dioxide is $^{13}C$-labeled carbon dioxide.

In other embodiments, the breath sample, or other bodily fluid sample, will be analyzed for the presence of isotopically labeled ammonia. Preferably, the isotopically labeled ammonia is $^{15}N$-labeled ammonia.

In certain embodiments, the breath sample, or other bodily fluid sample, will be analyzed for the presence of isotopically labeled carbon dioxide and isotopically labeled ammonia. Preferably, the isotopically labeled carbon dioxide is $^{13}C$-labeled carbon dioxide and the isotopically labeled ammonia is $^{15}N$-labeled ammonia.

In preferred analytic methods, the analysis step of the methods of the invention comprises comparing at least one ratio of isotopically labeled carbon dioxide, isotopically labeled ammonia, or a mixture thereof to non-isotopically carbon dioxide, non-isotopically labeled ammonia, or a mixture thereof in the breath sample of the patient after the administration of the isotopically-labeled citrulline to a control ratio of isotopically labeled carbon dioxide, isotopically labeled ammonia, or a mixture thereof to non-isotopically carbon dioxide, non-isotopically labeled ammonia, or a mixture thereof in the breath sample of the patient prior to the administration of the isotopically-labeled citrulline.

More preferably, the analysis step of the methods of the invention comprises comparing at least one ratio of isotopically labeled carbon dioxide to non-isotopically carbon dioxide in the breath sample of the patient after the administration of the isotopically-labeled citrulline to a control ratio of isotopically labeled carbon dioxide to non-isotopically carbon dioxide in the breath sample of the patient prior to the administration of the isotopically-labeled citrulline.

The methods of the invention are useful in identifying, for example, *Francisella tularensis*, and in particular, biovar A of *Francisella tularensis*, in the lungs of a patient or subject. *F. tularensis* presence can result in the development of pneumonic tularemia in a patient. Specifically, the present invention can be used to diagnose the presence of *Francisella tularensis* by the administration of a safe and effective amount of isotopically labeled citrulline and/or isotopically labeled glycerol, or a pharmaceutically acceptable salt of the citrulline and/or the glycerol, to a subject and then detecting the amount, for example, the concentration, of at least one of the cleavage or fermentation products of the isotopically labeled citrulline and/or isotopically labeled glycerol.

In the case of citrulline, detection of isotopically labeled ammonia and/or isotopically labeled carbon dioxide in the exhaled breath of the subject after a suitable period of time after administration (depending upon the route of administration) can provide diagnostic information about the existence of bacteria, for example, *F. tularensis*, or biovar Type A of *F. tularensis* in the subject's lungs.

In the case of glycerol, isotopically labeled carbon dioxide, isotopically labeled water, isotopically labeled propanediol, isotopically labeled ethanol or mixtures thereof, measured in the exhaled breath of the patient or subject, after a suitable time period has elapsed, can also provide diagnostic information about the existence of bacteria, for example, *F. tularensis*, or biovar Type A of *F. tularensis* in the subject's lungs.

In an alternative embodiment, isotopically labeled citrulline and/or isotopically labelled glycerol are administered to the subject to be tested for bacterial infection and, depending on the existence of isotopically labeled cleavage or fermentation products (or their absence) measured in the exhaled breath of the subject, diagnostic information may be used to determine whether or not there is a bacterial infection. Methods of the invention can be used to determine if *F. tularensis*, and in particular a biovar Type A or biovar Type B of *F. tularenesis* is present in the lungs of the subject.

In an aspect of the invention, in order to determine that an infection is present in the lungs, measurements of isotopically labeled nitrogen-15, carbon-13, hydrogen-2 and/or oxygen-17 or oxygen-18 in the breath of the tested subject are made and compared with concentrations of the naturally occurring nitrogen-14, carbon-12, hydrogen-1 and/or oxygen-16 in the breath of the tested subject for particular cleavage products. Preferably, at least a majority of the exhaled breaths, and most preferably every exhaled breath, is sampled for a given time period or until the determination of the level of activity has reached a preset accuracy.

A graph or curve may be generated showing the ratio of the isotopically labeled cleavage or fermentation product ("the isotopically labeled element") to the naturally occurring cleavage or fermentation product in the breath of the tested subject, as a function of time. A curve showing an increase in the ratio of the isotopically labeled element to non-isotopically labeled element over time is evidence of the existence of a bacterial infection. Using methods of the invention, a *F. tularensis* infection, in particular biovar Type A of *F. tularensis*, for example, can be detected.

An exemplary graph generated by comparing the ratio of isotopic nitrogen, carbon, oxygen and/or hydrogen in cleaved products in the exhaled breath of the patient can be made. By way of example, a graph of nitrogen-15/nitrogen-14 in ammonia, carbon-13/carbon-12 and/or oxygen-16/oxygen-18 or oxygen-17 in carbon dioxide, hydrogen-2/hydrogen-1 and/or oxygen-16/oxygen-18 or oxygen-17 in water, carbon-13/carbon-12 and/or oxygen-16/oxygen-18 or oxygen-17 in propanediol and/or ethanol in the exhaled breath of the subject to be diagnosed is/are made. The concentrations or amounts (ratio) of isotopically labeled elements in cleavage products are compared to a standard concentration (ratio) of those same cleavage products in a healthy patient and a curve is generated. From the curve, the presence or absence of *F. tularensis* biovar A may be determined or diagnosed directly. In the absence of *F. tularensis* biovar A (determined from the analysis above) and the presence of other symptoms or conditions of pneumonia tularemia, the presence of *F. tularensis* biovar B may determined or diagnosed indirectly.

A curve may be fitted to these measured concentrations and is then analyzed, preferably by determining the rate of rise of the curve. Such an analysis (rising rate) indicates the level of activity of *F. tularensis*, in particular biovar A in the subject, which can be used to diagnose the presence and extent of infection of *F. tularensis*, biovar A in the lungs of the patient. Alternatively, the absence of a rise in measured concentration in comparison to standard, along with symptoms of pneumonic tularemia will indicate the presence of *F. tularensis*, biovar B. This same approach may be used, with modification, to determine the effectiveness of therapy of a *F. tularensis* infection and the prognosis for inhibition and/or a cure of infection.

Examples of appropriate labels for the substrate, and hence for the cleavage product or products, are those which can be detected by an appropriate measuring instrument, but which are substantially not harmful or toxic to the subject including, but not limited to, carbon-13 or carbon-14, oxygen-18 (oxygen-17) or nitrogen-15, hydrogen-2 isotope-labelling.

An isotope is a form of an element, such as carbon, with a specific mass. For example, carbon-12 has a mass of 12 atomic mass units. In the present invention, the naturally more abundant isotope of each of these elements is at least partially replaced by a less abundant isotope. For example, the naturally more abundant carbon-12 atoms could be at least partially replaced by the less abundant carbon-13 atoms, permitting the cleavage product or products which carry the label to be more easily detected, since the less abundant isotope can be distinguished from the naturally more abundant isotope. Furthermore, the advantage of certain isotopes such as carbon-13 is that they are stable, so that they are not radioactive, unlike isotopes such as carbon-14. Therefore, preferably stable, non-radioactive isotopes such as carbon-13 are used as labels.

Compositions for oral administration or pulmonary administration are as otherwise described herein. Oral compositions include powders or granules, suspensions or solutions in water or non-aqueous media, sachets, capsules or tablets. Thickeners, diluents, flavorings, dispersing aids, emulsifiers or binders may be desirable. Such compositions adapted for oral administration can also include an enteric coating. Compositions for pulmonary administration include a pharmaceutically acceptable carrier, additive or excipient, as well as a propellant and optionally, a solvent and/or a dispersant to facilitate pulmonary delivery to the subject.

Following the step of administering the isotopically labeled citrulline and/or isotopically labeled glycerol to the subject, the exhaled breath of the subject is analyzed to detect an amount of isotopically labeled cleavage product or products as otherwise described herein, which indicate the presence of bacteria, for example, *F. tularensis* in the lungs of the subject. The amount of isotopically labeled product or products are detected by analyzing a gas sample of the exhaled breath of the subject with a measuring instrument. Such a gas sample can be obtained in a number of ways including, but not limited to, having the subject exhale or blow into a tube connected to the measuring instrument. Preferably, a nasal cannula is used. Such a cannula includes a section of tubing, usually plastic, with two prongs. Each prong is inserted into a nostril and the cannula is then connected to the measuring instrument. As the patient exhales through the nose, the exhaled air flows through the cannula to the measuring instrument.

The type of measuring instrument used to detect the isotopically labeled product or products depends upon the type of label. For example, if a carbon-13 isotopically-labelled substrate is used, the carbon-13 isotopically-labelled cleavage product or products can be detected by using a measuring instrument including, but not limited to a mass spectrometer or a gas analyzer, which is sensitive to the carbon-13 isotope. This is true for the other labels used (Nitrogen-15, oxygen-18 or H-2). By way of nonlimiting example (and as applied to the other elements by analogy), the ratio of the concentration of carbon-13 isotopically-labelled cleavage product or products to the concentration of carbon-12 cleavage product or products is then determined. Since carbon-12 is the more abundant isotope in nature, carbon-12 atoms are more abundant in unlabelled molecules. Thus, a higher carbon-13/carbon-12 ratio indicates a higher concentration of the carbon-13 isotopically-labelled cleavage product or products, which positively indicates the presence of *F. tularensis* in the lungs of the subject.

In certain preferred aspects of the invention, at least one of the cleavage products is carbon-13 isotopically-labelled carbon dioxide. Examples of measuring instruments which can be used with carbon-13 isotopically-labelled carbon dioxide include, but are not limited to, an infrared spectrometer. These infrared spectrometers are well known in the art, and have the advantage of being both rapid and accurate, as well as sensitive. Examples of such infrared spectrometers are disclosed in U.S. Pat. No. 5,063,275, herein incorporated by reference.

Alternatively, an analytical assay is described which is based on the use of C-13 labeled expired $CO_2$ as measured in the present assay. In this method isotope ratio mass spectroscopy (IRMS) is used as a detection method for C-13, a non-radioactive isotope that occurs naturally in food and animal tissues. Non-dispersive infrared spectroscopy (NDIRS) analysis and analysis methods which are well known in the art may be employed. The test protocol is as follows: isotopically labeled citrulline and/or glycerol is administered a subject or patient. The administration may be by oral or preferably by pulmonary administration, using an inhaler or other device adapted to deliver an effective amount (generally, an effective amount within the range of about 0.1 to about 10 mg, about 0.25 to about 5 mg, about 0.5 to about 2.5 mg. of isotopically labeled citrulline and/or glycerol, including both isotopically labeled citrulline and glycerol to the lungs of the patient or subject. After an appropriate period of time to allow any bacteria, for example, *F. tularensis*, within the lungs of the subject to convert the isotopically labeled citrulline and/or isotopically labeled glycerol to a cleavage product. Breath samples are collected before the dose and then a number of hours after administration of the citrulline and/or glycerol reflecting the conversion of substrate to cleavage product, and the isotopically labeled cleavage product in exhaled breath from the subject will be measured by an IRMS method.

Advantages of this test include, but are not limited to the following: it is practical, sensitive and specific; the validity of the test is not influenced by stress, exercise, hormone imbalances, or some drugs and medications it is a non-invasive method; it is simple to perform and can be readily used in physicians' offices or medical laboratories; it is safe since carbon-13 is a naturally occurring isotope found in all carbon-containing substances; it involves no radioactivity, and may be used in children and women.

Alternatively and preferably, at least one of the cleavage products is nitrogen-15 isotopically labeled ammonia. Of course, both carbon-13 isotopically labeled carbon dioxide and nitrogen-15 isotopically-labelled ammonia could be present, providing that the substrate has both labels. Both ammonia and carbon dioxide have the advantage of being molecules which are present in the exhaled breath of the subject.

In any case, the measuring instrument used to detect the cleavage product or products desirably have a number of characteristics. The measuring instrument must be able to measure the concentration of the product or products extremely rapidly. Furthermore, either the measuring instrument itself, or an associated device, must be able to perform the associated analysis, including both the fitting of the curve and the analysis of the curve. Such analyses must be performed rapidly. Preferably, the measuring instrument, alone or in conjunction with the associated device, should be able to measure the concentration and perform the associated analysis within about 10 seconds, and most preferably within about 3 seconds, particularly if substantially every exhaled breath of the subject is to be analyzed.

The term "suitable time period" refers to the length of time required for a cleavage product or products to form and to be exhaled in the breath of the subject. Thus, a number of events must occur. First, the administered isotopically labeled citrulline and/or isotopically labeled glycerol must be accessible to the bacterial, for example, *F. tularensis*. Then, the administered isotopically labeled citrulline and/or isotopically labeled glycerol must be cleaved or acted on by citrulline ureidase or glycerol fermentation of *F. tularensis* to form a cleavage product or products. The cleavage product or products must be produced in the lungs or alternatively, in the blood such that the cleavage product makes its way to the lungs in sufficient quantities. Next, the cleavage product or products must be exhaled in the breath of the subject. Finally, the presence of the cleavage product or products must be detected in the exhaled breath.

Furthermore, the "suitable time period" should be such that the curve of measured concentrations of cleavage product or products in the exhaled breath of the subject is substantially linear. Generally, the concentration will rise rapidly initially so that the fitted curve is substantially linear, and will then plateau after a period of time (preferably no more than about 40-70 minutes), as the process of formation and exhalation of cleavage product or products reaches a steady state. Eventually, as the administered urea is cleaved, the concentration will decrease. The analysis is preferably performed before the curve of measured values reaches a plateau.

This fitting and analysis of a curve of measured concentrations is useful for rapidly establishing the existence of a bacterial infection, for example *F. tularensis*, in particular a biovar A *F. tularensis* infection, in the lungs of the subject. The method of the present invention allows repeated breath samples to be rapidly obtained and then maximizes both the speed and the accuracy of analysis by fitting the measured values to a curve and then calculating the rate of increase of the curve, which is the derivative and which provides information as the existence and extent of infection.

Any method for identifying the concentration of isotopically labeled ammonia, isotopically labeled carbon dioxide (from cleavage of citrulline) or isotopically labeled ammonia, isotopically labeled carbon dioxide, isotopically labeled propanediol, isotopically labeled ethanol (from fermentation of glycerol) can be used to determine the existence (or absence) of a bacterial infection, for example, a *F. tularensis* infection, in the lungs of a patient or subject. The measurement of isotopically labeled gas (or liquid propane diol and/or ethanol in blood) as a cleavage product by action of the bacteria, for example, *F. tularensis*, on isotopically labeled citrulline and/or isotopically labeled glycerol directly evidences the existence (or absence) of a biovar of the bacteria, for example, biovar A *F. tularensis* in the lungs of the subject or the existence (or absence) of biovar B *F. tularensis* coupled with other symptoms of or analysis of *F. tularensis*.

In the present invention it is preferred to determine a ratio of an isotopically labeled element (carbon, nitrogen, oxygen, hydrogen) to a non-isotopically labeled element in a cleavage product (preferably gas) being analyzed. For example, if isotopically labeled ammonia is being measured as a cleavage product pursuant to citrulline administration, a ratio of nitrogen-15 to nitrogen-14 in ammonia obtained from the breath of a subject is determined. This may be determined readily using mass spectroscopy or infrared laser spectroscopy. For example, in preferred aspects of the invention, a ratio of nitrogen-15 to nitrogen-14 in ammonia exhaled by a subject to be diagnosed before administration of isotopically labeled citrulline is determined as a baseline ratio or standard. This ratio is generally below 1%.

Specifically, an exemplary method of analysis involves the following steps. A plurality of samples of exhaled breath of the subject is collected rapidly, on the order of one sample about every few seconds or so, preferably such that at least a majority, and most preferably substantially all of the exhaled breaths of the subject are sampled. Next, the concentration of a cleavage product is measured and the concentration of an isotopically labeled element, such as nitrogen-15, carbon-13, oxygen-17 or oxygen-18 or hydrogen-2 is compared with its naturally occurring counterpart (e.g. respectively, nitrogen-14, carbon-12, oxygen-16 and hydrogen-1) in the breath of the subject. Where the ratio of isotopically-labeled element to naturally occurring element is 0 or close to zero, then bacteria, for example, *F. tularensis* is not present. In cases where the ratio of isotopically-labeled element to naturally occurring element increases as a function of time, then the existence of bacteria, for example, *F. tularensis* is made out. A curve is fitted to the measured concentrations. If the ratio remains flat at the x-axis (essentially 0 or close to 0) as a function of time, the presence of bacteria, for example, *F. tularensis* is ruled out. The rate of rise of the curve may calculated by calculating the integral or by derivation (calculation of the derivative), preferably after the measurement of the concentration of cleavage product(s) in each sample. The analysis of the curve indicates the level of bacteria, for example, *F. tularensis* activity in the lungs of the subject. A rapid rise in the measured concentrations (a steeper curve), would evidence a high level of bacteria, for example, *F. tularensis* activity in the subject, whereas a slower rise in the measured concentrations (a shallower curve) would evidence a lower level of bacteria, for example, *F. tularensis* activity. Analogous approaches for providing the same information are also contemplated.

For example, in an analogous manner, if isotopically labeled citrulline and isotopically labeled glycerol (preferably having different elements labeled so that cleavage products of citrulline will be distinguishable from cleavage products of glycerol) are used, these can provide evidence of the existence (or absence) of *F. tularensis* produce concentrations of cleavage products which evidence that these substrates are being cleaved.

The calculation of a derivative has a number of advantages over other methods of analysis, such as the calculation of an integral. First, the calculation of the derivative does not require a reference breath sample to be obtained before isotopically labeled citrulline or isotopically labeled glycerol is administered to the subject. Since the derivative represents the rate of increase of the measured concentrations of a cleavage product or products, the starting concentration of that cleavage product or products is unimportant. However, the initial concentration of the cleavage product or products in the reference breath sample is important for the proper calculation of the integral, since such an initial concentration represents a background value which must be subtracted from the measured concentrations after administration of the substrate.

After the resultant measurement has reached a predetermined level of accuracy, or after a predetermined time period has elapsed, no more samples are collected.

The present method utilizing a breath assay has a number of advantages. For example, the exhaled breath of the subject can be analyzed in real time; that is, there is relatively little delay between the time the bacterial activity, for example, *F. tularensis* activity takes place, and the time such activity is measured. Second, the samples of exhaled breath are obtained rapidly and are analyzed immediately in a manner which substantially increases the accuracy of the results. Third, since multiple samples preferably are obtained, the accuracy of the test is increased. Fourth, there is less statistical error since many samples are collected. Fifth, since samples are preferably collected until a preset level of accuracy is reached, ambiguous results can be substantially eliminated, preventing the need for repeating the test.

The readout of isotopic ratios can be performed by sensitive gas mass spec analysis, but also laser spectroscopy techniques which may allow for more compact and portable devices.

Isotopically labeled citrulline and/or isotopically labeled glycerol may be administered by oral or preferably, by a pulmonary route of administration. Most preferably, the isotopically labeled citrulline and/or isotopically labeled glycerol is inhaled by the patient.

The pharmaceutical compositions of the invention for pulmonary administration are usually used as an inhalant. The compositions can be formed into dry powder inhalants, inhalant suspensions, inhalant solutions, encapsulated inhalants and like known forms of inhalants. Such forms of inhalants can be prepared by filling the pharmaceutical compositions of the invention into an appropriate inhaler such as a metered-dose inhaler, dry powder inhaler, atomizer bottle, nebulizer etc. before use. Of the above forms of inhalants, powder inhalants may be preferable.

When the pharmaceutical compositions of the invention are used in the form of a powder, the mean particle diameter of the powder is not especially limited but, in view of the residence of the particles in the lungs, is preferably in the range of about 0.1 to 20 µm, and particularly about 1 to 5 µm, because that size results in deep penetration of the particles within the lungs of the subject. Although the particle size distribution of the powder pharmaceutical compositions of the invention are not particularly limited, it is preferable that particles having a size of about 25 µm or more account for not more than about 5% of the particles, and preferably, 1% or less to maximize delivery into the lungs of the subject.

The pharmaceutical compositions in the form of a powder of the invention can be produced by, for example, the drying-micronization method, the spray drying method and the like.

According to the drying-pulverization method, the pharmaceutical compositions in the form of a powder can be prepared by drying an aqueous solution (or aqueous dispersion) containing a pharmacologically active substance and carrageenan and microparticulating the dried product. Stated more specifically, after dissolving (or dispersing) carrageenan in an aqueous medium, a pharmacologically active substance is added and dissolved (or dispersed) by stirring using a homogenizer, etc. to give an aqueous solution (or aqueous dispersion). The aqueous medium may be water alone or a mixture of water and a lower alcohol. Examples of usable lower alcohols include methanol, ethanol, 1-propanol, 2-propanol and like water-miscible alcohols. If glycerol is to be used as a substrate, ethanol may be used, but must be eliminated from the final formulation so as not to jeopardize measurements of ethanol from glycerol fermentation. After the obtained aqueous solution (or aqueous dispersion) is dried by blower, lyophilization, etc., the resulting product is pulverized or microparticulated into fine particles using jet mills, ball mills or like devices to give a powder having the above mean particle diameter. If necessary, additives as mentioned above may be added in any of the above steps.

According to the spray-drying method, the pharmaceutical compositions in the form of a powder of the invention can be prepared, for example, by spray-drying an aqueous solution (or aqueous dispersion) containing a pharmacologically active substances and excipients, additives or carriers for microparticulation. The aqueous solutions (or aqueous dispersion) can be prepared following the procedure of the above drying-micronization method. The spray-drying process can be performed using a known method, thereby giving a powdery pharmaceutical composition in the form of globular particles with the above-mentioned mean particle diameter.

The inhalant suspensions, inhalant solutions, encapsulated inhalants, etc. can also be prepared using the pharmaceutical composition in the form of a powder produced by the drying-micronization method, the spray-drying method and the like, or by using carrageenan and a pharmacologically active substance that can be administered via the lungs, according to known preparation methods.

Furthermore, the inhalant comprising the pharmaceutical compositions of the invention are preferably used as an aerosol. The aerosol can be prepared, for example, by filling the pharmaceutical composition of the invention and a propellant into an aerosol container. If necessary, dispersants, solvents and the like may be added. The aerosols may be prepared as 2-phase systems, 3-phase systems and diaphragm systems (double containers). The aerosol can be used in any form of a powder, suspension, solution or the like.

Examples of usable propellants include liquefied gas propellants, compressed gases and the like. Usable liquefied gas propellants include, for example, fluorinated hydrocarbons (e.g., CFC substitutes such as HCFC-22, HCFC-123, HFC-134a, HFC-227 and the like), liquefied petroleum, dimethyl ether and the like. Usable compressed gases include, for example, soluble gases (e.g., carbon dioxide, nitric oxide), insoluble gases (e.g., nitrogen) and the like.

The dispersant and solvent may be suitably selected from the additives mentioned above. The aerosol can be prepared, for example, by a known 2-step method comprising the step of preparing the composition of the invention and the step of filling and sealing the composition and propellant into the aerosol container.

As a preferred embodiment of the aerosol according to the invention, the following aerosol can be mentioned: Examples of the compounds to be used include isotopically labeled citrulline, isotopically labeled glycerol or mixtures thereof. Excipients and additives include carageenan, and those mainly comprising iota-carrageenan are preferable. As propellants, fluorinated hydrocarbons such as HFC-134a, HFC-227 and like CFC substitutes are preferable. Examples of usable solvents include water, ethanol, 2-propanol and the like. Water and ethanol are particularly preferable for citrulline and should be minimized or avoided when glycerol is included. In particular, a weight ratio of water to ethanol in the range of about 0:1 to 10:1 may be used for citrulline formulation. Formulations which comprise glycerol should substitute isopropanol for ethanol to avoid any impact on analysis (glycerol is fermented to ethanol in certain aspects of the invention).

The aerosol of the invention may contain carrageenan in an amount of about 0.01 to $10^4$ wt. % (preferably about 0.1 to about $10^3$ wt. %), propellant in an amount of about $10^2$ to $10^7$ wt. % (preferably about $10^3$ to $10^6$ wt. %), solvent in an amount of about 0 to $10^6$ wt. % (preferably about 10 to $10^5$ wt. %), and dispersant in an amount of 0 to $10^3$ wt. % (preferably about 0.01 to $10^2$ wt. %), relative to the weight of pharmacologically active substance.

The pharmaceutical compositions of the invention are safe and effective for use in the diagnostic methods according to the present invention. Although the dosage of the composition of the invention may vary depending on the type of active substance administered (isotopically labeled citrulline, isotopically labeled glycerol or mixtures thereof) as well as the nature (size, weight, etc.) of the subject to be diagnosed, the composition is administered in an amount effective for allowing the pharmacologically active substance (substrate) to be cleaved/fermented to cleavage products to be measured. For example, the composition is preferably administered such that the active ingredient can be given to a human adult in a dose of about 0.001 to about 100 mg, about 0.01 mg to about 25 mg, about 0.05 mg to about 15 mg, about 0.1 mg to about 10 mg, about 0.5 mg to about 5 mg, about 1 to about 3 mg, administered in a single dose.

The form of the pharmaceutical compositions of the invention such as a powder, solution, suspension etc. may be suitably selected according to the type of substance to be administered and the action of a target enzyme on the isotopically labeled active compound(s).

As an administration route, direct inhalation via the mouth using an inhaler is usually preferable. Since the pharmaceutical compositions of the invention allow direct local administration into the airways and in particular, directly to pulmonary tissue, the active substance contained therein produces immediate effects. Furthermore, the composition is formulated as an immediate release product so that cleavage and analysis can begin soon after administration.

The present invention allows rapid diagnosis of a bacterial infection, for example, a *F. tularensis* infection, in a patient or subject. The diagnosis is rapid and effective and displays a number of ancillary advantages as well, include direct diagnosis of perhaps a more virulent form of the bacteria, for example, biovar A *F. tularensis*, The present invention also allows the indirect diagnosis of, for example, *F. tularensis* biovar B, when coupled with other diagnostic and/or analytical methods.

The present invention also allows for the monitoring of a bacterial infection, for example, an *F. tularensis* infection, in the lungs of a patient, during therapy to determine the impact that an antibiotic regimen is having on resolving the bacterial infection.

The present invention represents a rapid, one-stop, easily administered test. The present approach of obtaining a sample from the lungs of the patient and processing the sample to determine the existence of a bacterial infection, for example, an *F. tularensis* infection, is laborious, time consuming and not cost effective. The prior art approach creates logistical issues, especially given that the risk element and principal use of the technology is anticipated to be to identify bioweaponized bacterial infections, for example, an *F. tularensis* infection. The present diagnostic test would be administered in a manner which would obviate the need for precise skill (compared to PCR and other diagnostic approaches) and would reduce/remove laboratory error/chain of custody concerns and the increased likelihood of infection of laboratory personnel. The present systems allow faster treatment of infected and potentially infectious patients. Finally, administration of a tracer tablet and collecting breath or urine afterwards needs lower level medical skills, making widespread testing by paramedics possible. Samples can easily be mailed to central facilities.

The present invention allows for the monitoring of therapy for a bacterial infection, for example, an *F. tularensis* infection. This is potentially quite useful for "in the field" applications. Thus, the present method not only can identify a bacterial infection, for example, an *F. tularensis* infection, with great accuracy, but can monitor the progression of therapy so that steps can be taken to modify a therapeutic regimen (for example, by adding an additional antibiotic or placing the patient on alternative therapy) for a more successful outcome.

In preferred embodiments, breath samples from a patient who has been administered isotopically labeled citrulline can be analyzed for isotopically labeled carbon dioxide and/or isotopically labeled ammonia after less than 8 hours post isotopically labeled citrulline administration. Preferably, analysis can be performed after less than 6 or 4 hours post isotopically labeled citrulline administration. Even more preferably, analysis can be performed after less than 2 or 3 hours post isotopically labeled citrulline administration. Most preferably, analysis can be performed after less than 1 hour post isotopically labeled citrulline administration. In most preferred embodiments, analysis can be performed after less than 45 minutes, 30 minutes, 20 minutes, 15 minutes, 10 minutes, or 5 minutes post isotopically labeled citrulline administration.

Also within the scope of the invention are kits useful for practicing the methods of the invention. Kits according to the invention comprise at least one unit dosage of isotopically labeled citrulline or a pharmaceutically acceptable salt thereof, and at least one device for the delivery of the isotopically labeled citrulline to a patient or at least one breath collection device or a combination of such devices. Kits of the invention can include a unit dosage form comprising a single use container and a diagnostically effective amount of isotopicaly labeled citrulline, or a pharmaceutically acceptable salt thereof, in combination with a pharmaceutically acceptable carrier, additive, or excipient. The delivery devices used within the kits of the invention can be any one or more of the delivery devices described herein or known to those skilled in the art. Preferred delivery devices include inhalers.

Breath collection devices for use with the kits of the invention include any of the collection devices described herein or known to those skilled in the art. Preferred collection devices include bags and vials.

Kits of the invention can optionally include instructions for using the kits of the invention. These instructions will preferably describe how to use the kit to assay for the presence or absence of a bacterial lung infection in a patient.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the present invention.

The following terms shall be used to describe the present invention. In instances where a term is not defined specifically, that term shall be accorded the ordinary meaning ascribed to the term by those of ordinary skill in the art when used within context.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The term "patient or subject" refers to a human or domesticated animal, on whom the method of diagnosing an infection of the lungs is performed.

The term "natural abundance" refers to the amount of an isotope, for example, $^{13}C$, $^{14}C$, $^{17}O$, $^{18}O$, and $^{15}N$, as naturally found on earth. Isotopes present in the isotopically labeled compounds of the invention are understood to have been incorporated using synthetic techniques known in the art. For example, the natural abundance of $^{13}C$ is about 1.1%. $^{14}C$ exists in nature in only trace amounts. The natural abundance of $^{18}O$ is about 0.2%. The natural abundance of $^{17}O$ is about 0.04%. The natural abundance of $^{15}N$ is about 0.36%.

As used herein, "unit dosage" refers to a pre-determined amount of a pharmaceutical composition or compound of the invention.

The term "pneumonic tularemia" is used to describe a particular disease state or condition caused by the infectious agent *Francisella tularensis*, which is a small, rod-shaped nonmotile bacteria. *F. tularensis* has been found in over 100 species of mammals, birds, amphibians, arthropods, and even fish, and the disease occurs throughout North American and Eurasia. It is most prevalent in the western and south-central parts of the country. Typically, a few hundred cases of tularemia are reported in the U.S. every year. Although relatively rare in nature, pneumonic tularemia is feared to be a disease caused by bioweaponized *F. tularensis*.

The main vectors of *F. tularensis* are small mammals such as mice, moles, squirrels, rabbits and hares. Small mammal vectors usually acquire the organism through the bite of an infected tick or other arthropod or by contact with contaminants in the environment, noting that the microbe can survive for a number of weeks outside of a living host. In humans, infection is usually caused by bites from *Dermacentor* or *Amblyomma* ticks in summer and from contact with rabbit carcasses in winter, but other modes of transmission occur, especially contact with contaminated water, air or soil.

There are several different types of tularemia, which vary in presentation and severity depending on the method of acquisition and the dose and virulence of the specific infecting organisms. Typically, tularemia is divided into six forms:

ulceroglandular, oculoglandular, glandular, oropharyngeal, typhoidal and pneumonic. Of these, typhoidal tularemia is the most serious form.

Pneumonic tularemia commonly develops by inhalation of *F. tularensis*, but can occur as a consequence of ulceroglandular tularemia from a bite by a tick or from abrasion, as a secondary disease state. Pneumonic tularemia may also develop as a consequence of typhoid tularemia (septicemia tularemia), also as a secondary disease state.

Because *F. tularensis* can exist in aerosolized form and as few as 10-50 organisms are required to establish infection and cause disease, there is increasing concern that tularemia could be used as a bioweapon.

Symptoms of tularemia usually develop within three or four days of infection, although in some cases it can take up to 10 days for the disease to manifest. The organism is intracellular and spreads via the lymphatic system, multiplying within macrophages. Pneumonic tularemia is characterized by fever, exhaustion and weight loss accompanied by lung infection. Typically, the patient experiences a dry cough, respiratory difficulty and chest pain. Meningitis is an uncommon but potentially serious complication of tularemia.

Diagnosis of tularemia is based on the signs and symptoms described above, ideally combined with a history of recent arthropod bite or plausible environmental exposure to *F. tularensis*. Standard blood tests have historically been unhelpful in diagnosing tularemia, although about half of all patients will exhibit non-specific abnormalities in liver function. Some patients develop elevated creatine kinase levels as a result of rhabdomyolosis; this is frequently associated with a poor prognosis.

A number of specific tests exist for tularemia, but they are not widely available. Direct examination of biopsy specimens or secretions by fluorescent antibody or Gram or histochemical stains is often helpful in diagnosis. *F. tularensis* can also be demonstrated microscopically with fluorescent-labeled antibodies. Antibodies are not typically present, however in the first ten days to so after exposure. Polymerase chain reaction (PCR) tests can also be utilized. *F. tularensis* can be grown in culture, although such practice is somewhat risk in that workers can themselves become infected.

Traditional parenteral antibiotic therapy with streptomycin is the treatment of choice for tularemia. Gentamicin is considered an acceptable alternative. The recommended treatment period is about 7-10 days. Quinolone and fluoroquinolone (e.g., naldixic acid, ciprofloxacin, levofloxacin, trovofloxacin, norifloxacin, gemifloxacin, moxifloxacin, among others) are also effective against *F. tularensis*, thus providing an additional option for physicians. Tetracyclines and chloramphenicol can also be used, but a higher rate of relapse is associated with these agents, as they are bacteriostatic rather than bactericidal. Recommended treatment with these medications is usually extended to 2-3 weeks or more.

Although the mortality rate for tularemia is generally low, around 1-2%, the mortality rate for untreated pneumonic tularemia may be as high as one-third.

The term "compound" shall mean any specific compound which is disclosed within this specification and typically means an isotopically labeled compound. Pharmaceutically acceptable salts are also compounds for use in the present invention. The term compound, as it relates to the present invention, also refers to isotopically labeled citrulline and glycerol, as well as compounds/derivatives of these compounds.

The term "effective" when used in context, shall mean any amount of a compound or component which is used to produce an intended result within the context of its use. In the case of compounds according to the present invention, the term effective generally refers to an effective amount of citrulline and/or glycerol, which are isotopically labeled and administered to a patient or subject. In addition, a therapeutically effective amount of compound which will inhibit the growth and/or produce a die-off (bacteriacidal) of *F. tularensis*. This is distinguishable from a diagnostically effective amount of citrulline and/or glycerol which may be administered/used short term (for example, a few hours) to diagnose the presence of a *F. tularensis* infection in a patient at risk. Agents useful in treating pneumonic tularemia infections are treated with an amount and for a duration effective in treating (i.e., in eliminating or at least stabilizing) the infection in the patient.

The terms "agents," "active agents", "active compounds" "isotopically labeled active agents or compounds" describes, within context, isotopically labeled metabolic precursors in this case citrulline and/or glycerol which are acted on by enzyme pathways of *F. tularensis* to produce identifiable and distinguishable cleavage products or metabolites which can be analyzed using conventionally available analytic tools and methodologies. Active agents according to the present invention include citrulline, glycerol and their pharmaceutically acceptable salts. In the present invention, if a patient has a *F. tularensis* infection in his or her lungs, the isotopically labeled compound, which is delivered to the lungs is metabolized to at least one isotopically labeled cleavage product (which is preferably a gas) selected from the group ammonia, carbon dioxide, water, propanediol and ethanol. While propanediol and ethanol are liquids at ambient temperature, these compounds may be vaporized and measured using techniques as otherwise disclosed herein for the gaseous cleavage products, or alternatively, may be monitored in the blood of the subject.

The term "cleavage product of citrulline" refers, within context, to ammonia and carbon dioxide and the term "cleavage product of glycerol" refers, within context, to carbon dioxide, water, propanediol and/or ethanol.

The term "cleaves" refers to the fact that bacterial, for example, *F. tularensis*, in particular, biovar A, through enzymatic process (e.g., citrulline ureidase or fermentation) can break at least one chemical bond of citrulline and/or glycerol, forming a plurality of products, by a chemical process including, but not limited to, hydrolysis. A product so formed is a "cleavage or fermentation product". The concentration of the cleavage product or products indicates the level of activity of the bacteria, for example, *F. tularensis*, in the lungs of the patient or subject, which can be used to determine a diagnosis of infection. A positive diagnosis can also indicate the presence of a biovar in the lungs of the patient, for example, the present of *F. tularensis*, biovar A. A negative diagnosis in the presence other symptology of pneumonic tularemia may indicate the presence a different biovar that does not cleave citrulline or glycerol, for example, *F. tularensis*, biovar B. The method for diagnosis according to the present invention is referred to as a "breath test."

The term "safe and effective amount of substrate" refers to an amount of a substrate (i.e., isotopically labeled citrulline, isotopically labeled glycerol or mixtures of these two) which is sufficient to produce a detectable level of a cleavage product or products, without an untoward level of adverse side effects, such as toxicity, irritation, allergy or hypersensitivity responses. The level of any such side effects should be commensurate with acceptable risk/benefit ratios.

The term "isotope-labelling" is used to describe the naturally more abundant isotope of each of these elements is at least partially replaced by a less abundant isotope. For example, the naturally more abundant carbon-12 atoms could be at least partially replaced by the less abundant carbon-13 atoms, permitting the cleavage product or products which carry the label to be more easily detected, since the less abundant isotope can be distinguished from the naturally more abundant isotope. Furthermore, the advantage of certain isotopes such as carbon-13 is that they are stable, so that they are not radioactive, unlike isotopes such as carbon-14. Therefore, preferably stable, non-radioactive isotopes such as carbon-13, nitrogen-15, oxygen-17 or 18 and hydrogen-2 preferably are used as labels, depending upon the cleave product to be analyzed.

The following examples provide insight into the use of the present invention. The examples are simply that, exemplary, and are not to be construed to limit the present invention in any way.

Example 1

A patient is suspected of (pneumonic) lung tularemia as a result of a potential bioweapon release in a Gulf state. The patient inhales 1 to 100 mg of citrulline, with $^{13}$C-label on the ureide:

using a dry powder inhaler, and exhaled breath $^{13}CO_2$ levels monitored over then next 5 to 120 minutes. An increase in $^{13}CO_2$ breath concentrations after inhalation, above a threshold value to be determined, would support a diagnosis of pneumonic tularemia.

Example 2

A patient is suspected of (pneumonic) lung tularemia as a result of an accidental release in a research lab, and is critically ill on an incubator. The patient has a solution nebulized containing 1 to 100 mg of citrulline, with $^{13}$C-label on the ureide:

and exhaled breath $^{13}CO_2$ levels monitored over then next 5 to 120 minutes. An increase in $^{13}CO_2$ breath concentrations after inhalation, above a threshold value to be determined, would strongly support a diagnosis of pneumonic tularemia.

Example 3

*Francisella tularensis* strains Schu4, LVS and Holoarctica were grown to mid log phase, harvested, and sonicated at different powers (P08 to P10) or with bacterial protein extraction reagent (B-PER, Pierce) to release intracellular citrulline ureidase. Whole bacteria were removed by filtration, and lysate sterility assessed. The assay system consisted of phosphate buffered saline 700 ul, lytsate 50 ul and 250 ul of 1 mM ureido-$^{13}$C-citrulline.

The assay was incubated overnight, and headspace gas analysed for d$^{13}CO_2$ using isotope ratio mass spectrometry as previously (Jassal et al 2010, PloS One 27; 5 e12451). The following lysates, including the method used to release intracellular citrulline ureidase, were tested:

| Strain | Method |
|---|---|
| Schu S4 | PO8 |
| Schu S4 | PO9 |
| Schu S4 | PO10 |
| Schu S4 | B-PER |
| Schu S4 | B-PER |
| LVS | PO8 |
| LVS | PO9 |
| LVS | PO10 |
| LVS | B-PER |
| LVS | B-PER |
| *Holartica* | PO8 |
| *Holartica* | PO9 |
| *Holartica* | PO10 |
| *Holartica* | B-PER |
| *Holartica* | B-PER |

The results are shown in FIG. 1.

Example 4

Preparation of an Isotopically Labeled Citrulline 2 grams of l-ornithine sulfate were heated at reflux with an excess of copper oxide (1 gram) in 10 ml of distilled water for 10 minutes, producing a blue solution of copper-l-ornithine complex. Excess copper oxide was removed by filtration. The copper-l-ornithine complex was added to 1 gram $^{13}$C-urea in a 15 ml Q-tube, and reacted at 102° C. for 3 hours, forming a precipitate of copper-l-$^{13}$C-ureido-citrulline which was collected and washed with water (3 ml), and without isolation treated with an excess of $Al_2S_3$ to produce a clear solution free l-$^{13}$C-ureido-citrulline and a precipitate of copper sulfide which was removed by filtration and concentrated to 2 ml, and 10 ml of ethanol added and stored at 4° C. overnight for crystallization. Mp 220° C. uncorrected, TLC on silica using n-butanol-acetic acid-water 40:10:17, Rf 0.4, as was l-citrulline standard.

Some embodiments of the present invention include methods for diagnosing the presence of *Francisella tularensis* in the lungs of a patient or subject, including the steps of:

(a) administering an effective amount of at least one isotopically labeled agent selected from the group consisting of citrulline, glycerol, a pharmaceutically acceptable salt thereof or mixtures thereof to the patient or subject, said active compound being acted upon by *F. tularensis* if present to form an isotopically labeled cleavage product or fermentation product;

(b) collecting the breath, urine, whole blood, plasma or serum samples from the subject; and (c) analyzing said samples to determine a concentration or concentrations of said cleavage product(s) or fermentation product(s), said concentration(s) indicating the presence or absence of *F. tularensis* including the presence or absence of type A biovar of *F. tularensis* in the lungs of said patient or subject.

In some embodiments, said agent is citrulline or a pharmaceutically acceptable salt thereof. In other embodiments, said agent is a mixture of citrulline and/or a pharmaceutically acceptable salt of citrulline and glycerol.

In certain embodiments, said sample is the breath of said subject taken for a predetermined time.

In other embodiments, said agent is isotopically labeled with carbon-13, nitrogen-15, oxygen-17, oxygen-18, hydrogen-2 or mixtures thereof. In still other embodiments, said agent is citrulline or its pharmaceutically acceptable salt isotopically labeled with carbon-13, nitrogen-15, oxygen-17 or oxygen-18. In yet other embodiments, said citrulline is isotopically labeled with carbon-13 or nitrogen-15. In other embodiments, said citrulline is isotopically labeled with carbon-13.

In preferred embodiments of the invention, said agent is glycerol isotopically labeled with carbon-13, oxygen-17, oxygen-18, hydrogen-2 or mixtures thereof. Preferably, said glycine is isotopically labeled with nitrogen-15. In other embodiments, said glycerol is isotopically labeled with carbon-13, oxygen-17, oxygen-18, hydrogen-2 or mixtures thereof. In yet other embodiments, said glycerol is isotopically labeled with carbon-13 or oxygen-18.

In some embodiments, said cleavage product or said fermentation product is selected from the group consisting of ammonia, carbon dioxide, water and propanediol. In other embodiments, said cleavage product or fermentation product is a gas. Preferably, said gas is ammonia, carbon dioxide or mixtures thereof. Also preferred are embodiments wherein said gas is a mixture of isotopically labeled carbon dioxide, from the action of *F. tularensis* on citrulline and/or glycerol and isotopically labeled ammonia from the action of *F. tularnesis* on citrulline.

In some embodiments of the invention, said isotopically labeled cleavage product or metabolite is selected from the group consisting of propanediol, ethanol or mixtures thereof, which is measured in the urine, whole blood, serum or plasma of the patient.

In preferred embodiments of the invention, said analyzing step comprises comparing at least one ratio of isotopically labeled element(s) to non-isotopically labeled element(s) in said exhaled breath of said subject to a control ratio of isotopically labeled element(s) to non-isotopically labeled elements in the exhaled breath of said subject or a control group prior to administration of said isotopically labeled active agent.

In certain preferred embodiments of the invention, said agent is administered to the lungs by a pulmonary route. In other embodiments, said agent is administered orally.

Some embodiments of the invention include the optional steps of fitting the concentrations of said cleavage products obtained to a curve; and analyzing the curve or a plateau of said curve to determine the extent of infection.

Also within the scope of the invention are compositions adapted for pulmonary administration to a subject to be diagnosed for the existence or absence of bacterial infection in the lungs of a patient, said composition consisting essentially of a diagnostic effective amount of isotopically labeled citrulline and/or isotopically labeled glycerol, pharmaceutically acceptable salts or mixtures thereof, in combination with a pharmaceutically acceptable excipient, a propellant and optionally, a solvent and a dispersant, said composition being further adapted for single use only. In preferred compositions of the invention, said citrulline, glycerol or pharmaceutically acceptable salts or mixtures thereof are present in amounts ranging from about 0.25 mg to about 10 mg each in said composition. Preferred compositions are aerosols. Other preferred compositions are adapted for delivery through an inhaler. In some embodiments, said solvent is a mixture of water and ethanol and said propellant is a CFC substitute fluorinated hydrocarbon.

Also within the scope of the invention are single dose compositions adapted for oral administration to a subject, said composition consisting essentially of a diagnostic effective amount of isotopically labeled citrulline and/or isotopically labeled glycerol, or pharmaceutically acceptable salts and mixtures thereof, in combination with a pharmaceutically acceptable carrier, additive or excipient. Preferably, the composition has an enteric coating and is in enteric dosage form. In some embodiments, said citrulline and/or glycerol together comprise about 0.5 mg to about 100 mg by weight.

Also within the scope of the invention are kits comprising a single dose composition as disclosed herein, a bag or vial to collect the breath of a subject after administration of said composition; and an instruction manual. Preferably, the composition administered using the kits of the invention is administered using an inhaler.

What is claimed:

1. A method for diagnosing a presence or absence of a citrulline ureidase positive bacterial infection in the lungs of a patient comprising:
   administering a diagnostically effective amount of an isotopically-labeled citrulline, or a pharmaceutically acceptable salt thereof, to the lungs of the patient;
   collecting one or more breath, urine, whole blood, plasma, or serum samples from the patient; and
   analyzing the one or more samples to determine the amount of isotopically labeled carbon dioxide, isotopically labeled ammonia, or a mixture thereof in said samples;
   said amount indicating the presence or absence of the bacterial infection.

2. The method according to claim 1 wherein said sample is the breath of said patient taken for a predetermined time.

3. The method according to claim 1 wherein the sample is a predetermined volume of the breath of said patient.

4. The method according to claim 1 wherein the citrulline includes a plurality of isotopic labels.

5. The method according to claim 1 wherein the isotopic label is carbon-13, carbon-14, nitrogen-15, oxygen-17, oxygen-18, hydrogen-2, or a mixture thereof.

6. The method according to claim 1, wherein the isotopic label is carbon-13, nitrogen-15, oxygen-17, or oxygen-18.

7. The method according to claim 1 wherein the isotopic label is carbon-13 or nitrogen-15.

8. The method according to claim 1, wherein the isotopic label is carbon-13.

9. The method according to claim 1, wherein the sample is analyzed to determine the amount of isotopically labeled carbon dioxide.

10. The method according to claim 1, wherein the sample is analyzed to determine the amount of isotopically labeled ammonia.

11. The method according to claim 1 wherein said analyzing step comprises comparing
    at least one ratio of isotopically labeled carbon dioxide, isotopically labeled ammonia, or a mixture thereof to non-isotopically carbon dioxide, non-isotopically labeled ammonia, or a mixture thereof in the breath sample of the patient after the administration of the isotopically-labeled citrulline to a control ratio of isotopically labeled carbon dioxide, isotopically labeled ammonia, or a mixture thereof to non-isotopically carbon dioxide, non-isotopically labeled ammonia, or a mixture thereof in the breath sample of the patient prior to the administration of the isotopically-labeled citrulline.

12. The method according to claim 1 wherein said analyzing step comprises comparing at least one ratio of isotopically labeled carbon dioxide to non-isotopically carbon dioxide in the breath sample of the patient after the administration of the isotopically-labeled citrulline to a control ratio of isotopically labeled carbon dioxide to non-isotopically carbon dioxide in the breath sample of the patient prior to the administration of the isotopically-labeled citrulline.

13. The method according to claim 1 wherein said isotopically labeled citrulline is delivered to the lungs of the patient by pulmonary route of administration.

14. The method according to claim 1 wherein said isotopically labeled citrulline is delivered orally.

15. The method according to claim 1, further comprising optional steps of fitting the amount of said isotopically labeled carbon dioxide, isotopically labeled ammonia, or a mixture thereof to a curve; and analyzing the curve or a plateau of said curve to determine the extent of the bacterial infection.

16. The method of according to claim 1 wherein the bacterial infection is a *Francisella tularensis* infection.

17. The method of claim 16 wherein analysis of the amount of isotopically labeled carbon dioxide, isotopically labeled ammonia, or mixture thereof indicates the presence or absence of the Type A biovar of *F tularensis* in the lungs of said patient.

\* \* \* \* \*